US011185630B2

United States Patent
Inoue et al.

(10) Patent No.: US 11,185,630 B2
(45) Date of Patent: Nov. 30, 2021

(54) LIQUID LEAKAGE DETECTION DEVICE

(71) Applicant: Tatsuta Electric Wire & Cable Co., Ltd., Osaka (JP)

(72) Inventors: Junichi Inoue, Kyoto (JP); Hiroaki Umeda, Kyoto (JP)

(73) Assignee: Tatsuta Electric Wire & Cable Co., Ltd., Osaka (JP)

( * ) Notice: Subject to any disclaimer, the term of this patent is extended or adjusted under 35 U.S.C. 154(b) by 483 days.

(21) Appl. No.: 16/090,790

(22) PCT Filed: Oct. 14, 2016

(86) PCT No.: PCT/JP2016/080623
§ 371 (c)(1),
(2) Date: Oct. 2, 2018

(87) PCT Pub. No.: WO2017/179228
PCT Pub. Date: Oct. 19, 2017

(65) Prior Publication Data
US 2020/0324045 A1    Oct. 15, 2020

(30) Foreign Application Priority Data
Apr. 12, 2016   (JP) .............................. JP2016-079743

(51) Int. Cl.
*A61M 5/168*    (2006.01)
(52) U.S. Cl.
CPC .... *A61M 5/16831* (2013.01); *A61M 5/16836* (2013.01); *A61M 2205/15* (2013.01);
(Continued)
(58) Field of Classification Search
CPC ............................................... A61M 5/16836
See application file for complete search history.

(56) References Cited

U.S. PATENT DOCUMENTS

| 3,618,602 A | 11/1971 | Shaw |
| 4,010,749 A * | 3/1977 | Shaw ................ A61M 5/16836 |
| | | 604/503 |

(Continued)

FOREIGN PATENT DOCUMENTS

| JP | S49017717 B1 | 5/1974 |
| JP | 2007502148 A | 2/2007 |

(Continued)

OTHER PUBLICATIONS

International Search Report dated Dec. 27, 2016 filed in PCT/JP2016/080623.

(Continued)

*Primary Examiner* — Nilay J Shah
*Assistant Examiner* — Robert F Allen
(74) *Attorney, Agent, or Firm* — Rankin, Hill & Clark LLP

(57) ABSTRACT

To provide a liquid leakage detection device in which restriction of of a patient is alleviated as compared with the related art while receiving an injection. A liquid leakage detection device 2 detects that an injection solution to be injected into a blood vessel 4 leaks to the outside of the blood vessel 4. The liquid leakage detection device 2 includes a plurality of thermocouples 18 attached to a body surface around a puncture site 16 of an injection needle 12 for injecting the injection solution, an acquisition device 34 which acquires a value indicating a body surface temperature at an attachment point of each of the thermocouples 18 based on an output of each of the thermocouples 18, and a determination device 14 which determines that the injection solution leaks to the outside of the blood vessel when the acquired value deviates from a normal temperature of the body surface temperature at the attachment point.

4 Claims, 8 Drawing Sheets

(52) U.S. Cl.
CPC ..... *A61M 2205/18* (2013.01); *A61M 2205/52* (2013.01); *A61M 2230/50* (2013.01)

(56) References Cited

U.S. PATENT DOCUMENTS 6,979,306 B2 * 12/2005 Moll .................. A61B 5/02042
210/646
2005/0038325 A1   2/2005 Moll

FOREIGN PATENT DOCUMENTS

TW        200815060 A     4/2008
WO        2015034104 A1   3/2015

OTHER PUBLICATIONS

Chinese Office Action (CNOA) dated Jul. 22, 2020 for the corresponding Chinese Patent Application No. 201680084312.2 and its Partial English translation.

* cited by examiner

FIG. 7
(a)
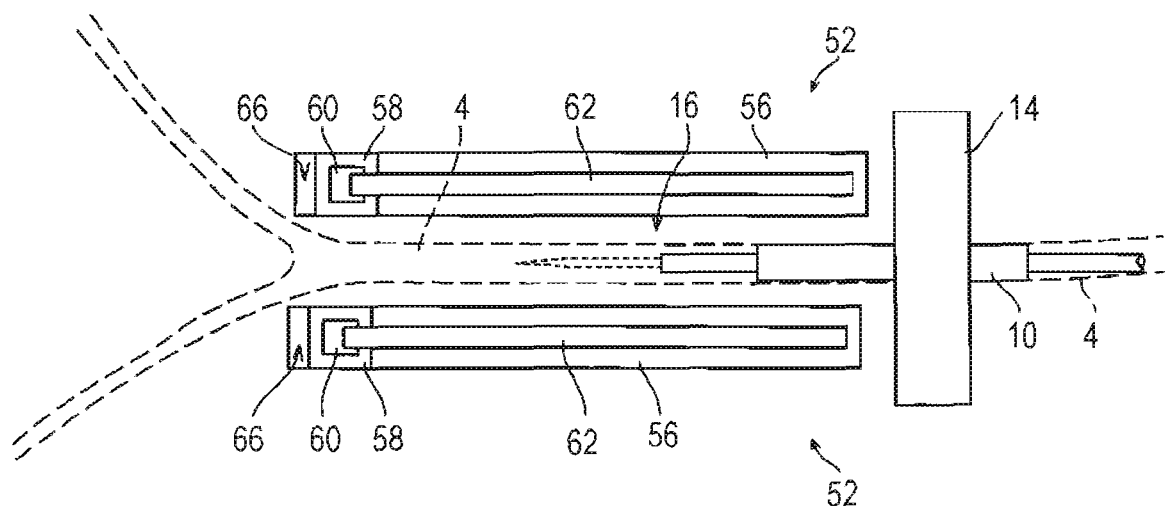
(b)
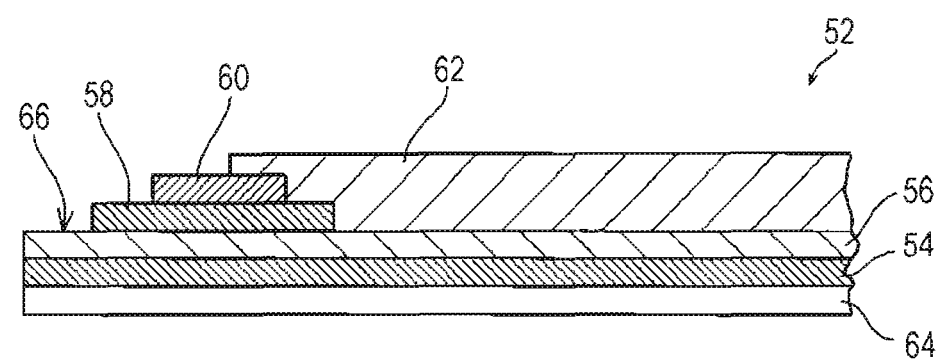

FIG. 8
(a)
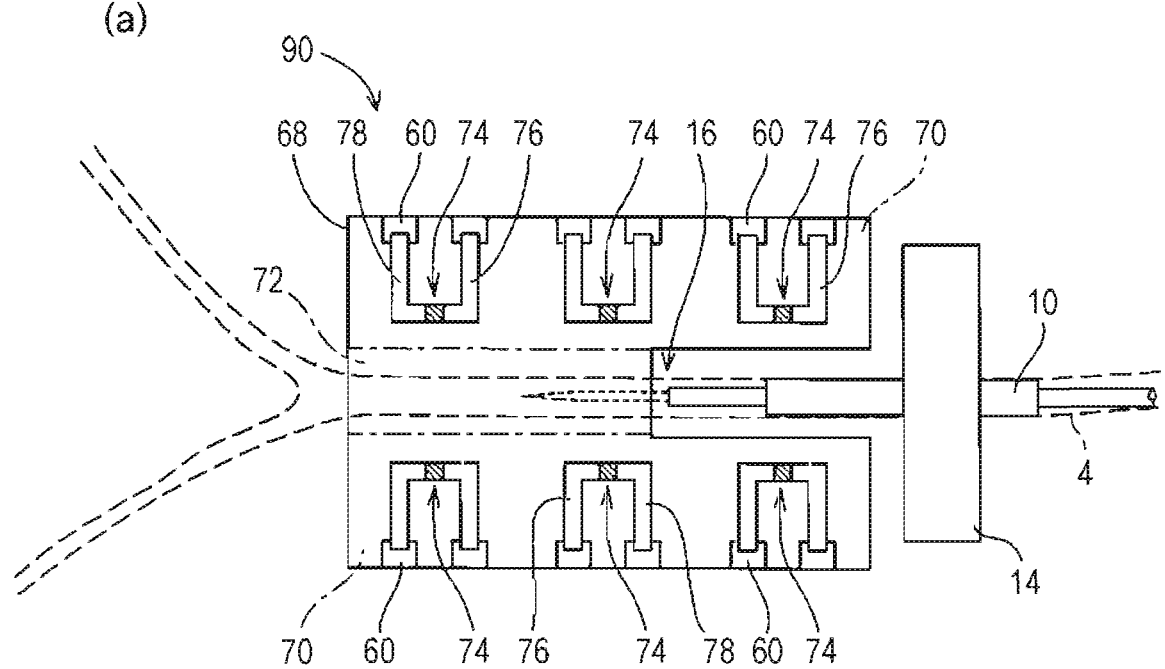
(b)
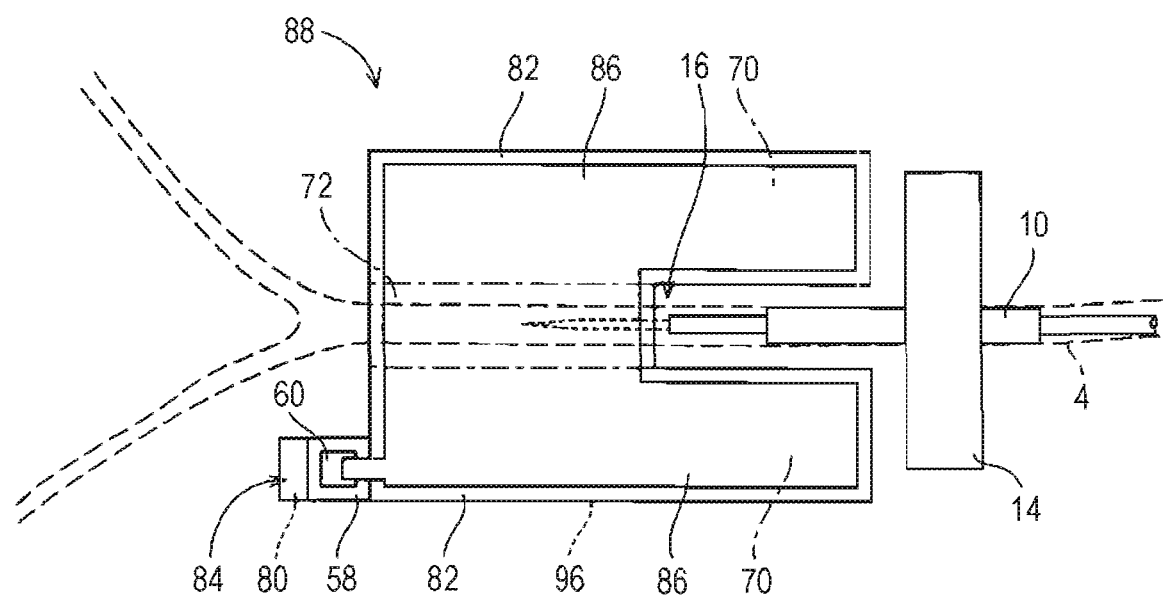

LIQUID LEAKAGE DETECTION DEVICE

TECHNICAL FIELD

The present invention relates to a liquid leakage detection device. The present invention especially relates to a device for detecting that an injection solution to be injected into a blood vessel leaks to the outside of the blood vessel.

BACKGROUND ART

For example, during administration of an injection solution to a patient by drip infusion, when a syringe is not securely fixed, or when the patient moves a puncture site, for example, an injection needle comes off from the blood vessel, or the injection needle pierces through the blood vessel, and thus a drug solution may not be normally injected into the blood vessel. For example, when so-called extravasation occurs in which an anticancer agent as the injection solution is not injected into the blood vessel but leaks into a body outside the blood vessel, and when its discovery is delayed, it leads to an accident such as a tissue necrosis at a leakage site.

In order to prevent such an accident, a technique for detecting occurrence of the extravasation is disclosed in Patent Literature 1. This technique is a detection technique using thermography. In this technique, a periphery of the puncture site is imaged by the thermography, and a body temperature within an imaging area is measured. When a temperature change exceeding a certain level occurs within the imaging range, it is determined that the extravasation has occurred and a warning device is activated.

CITATION LIST

Patent Literature

Patent Literature 1: WO 15/034104 A

SUMMARY OF THE INVENTION

Problems to be Solved by the Invention

However, since the thermography is a device for imaging the vicinity of the puncture site from a fixed point, for example when the patient moves inadvertently, the vicinity of the puncture site deviates from the imaging area and the body temperature cannot be measured. Further, even when the periphery of the puncture site is covered with clothing or bedding, the body temperature around the puncture site cannot be measured normally. Thus, the above-described technique imposes severe restrictions on imaging conditions where the extravasation can be detected. Therefore, with the restrictions, movement of the patient is limited beyond necessity while receiving the drip infusion.

The above-mentioned problems are common not only for anticancer agents but also for other injection solutions such as nutritional supplements.

An object of the present invention is to provide a liquid leakage detection device in which restriction of movement of a patient is alleviated as compared with the prior art while receiving an injection in view of the above-described problems.

Solution to the Problems

In order to achieve the above object, a liquid leakage detection device for detecting that an injection solution to be injected into a blood vessel leaks to the outside of the blood vessel according to the present invention, includes a heat-sensitive sensor attached to a body surface around a puncture site of an injection needle for injecting the injection solution, an acquisition device which acquires a value indicating a body surface temperature at an attachment point of the heat-sensitive sensor based on an output of the heat-sensitive sensor, and a determination device which determines that the injection solution leaks to the outside of the blood vessel when the acquired value deviates from a normal temperature of the body surface temperature at the attachment point.

Further, the present invention is the liquid leakage detection device further including a notification device which notifies that the injection solution leaks to the outside of the blood vessel when the determination device determines that the injection solution leaks to the outside of the blood vessel.

Furthermore, the present invention is the liquid leakage detection device, wherein the heat-sensitive sensor is a plurality of heat-sensitive elements, and the plurality of heat-sensitive elements is distributed and attached to both sides of the blood vessel into which the injection needle is punctured.

Effects of the Invention

According to the liquid leakage detection device of the present invention, the heat-sensitive sensor is attached to the body surface around the puncture site. Thus, the body surface temperature around the puncture site can be directly sensed. Therefore, even when the patient moves inadvertently, or even when the puncture site is covered with the bedding and the like, the body surface temperature can be normally sensed. Then, leakage of the injection solution is determined based on the body surface temperature. Therefore, a behavior of the patient receiving the injection is not limited beyond necessity.

BRIEF DESCRIPTION OF THE DRAWINGS

FIG. 7($a$) is a diagram showing a mode of attachment of a heat-sensitive element according to Modification, and FIG. 7($b$) is a cross-sectional view of the heat-sensitive element.

FIG. 8($a$) is a diagram showing a heat-sensitive sensor according to Modification, and FIG. 8($b$) is a diagram showing the heat-sensitive sensor according to Modification.

DESCRIPTION OF THE EMBODIMENTS

Embodiments of a liquid leakage detection device according to the present invention will be described in detail below with reference to the drawings.

Embodiment 1

Figure 1:
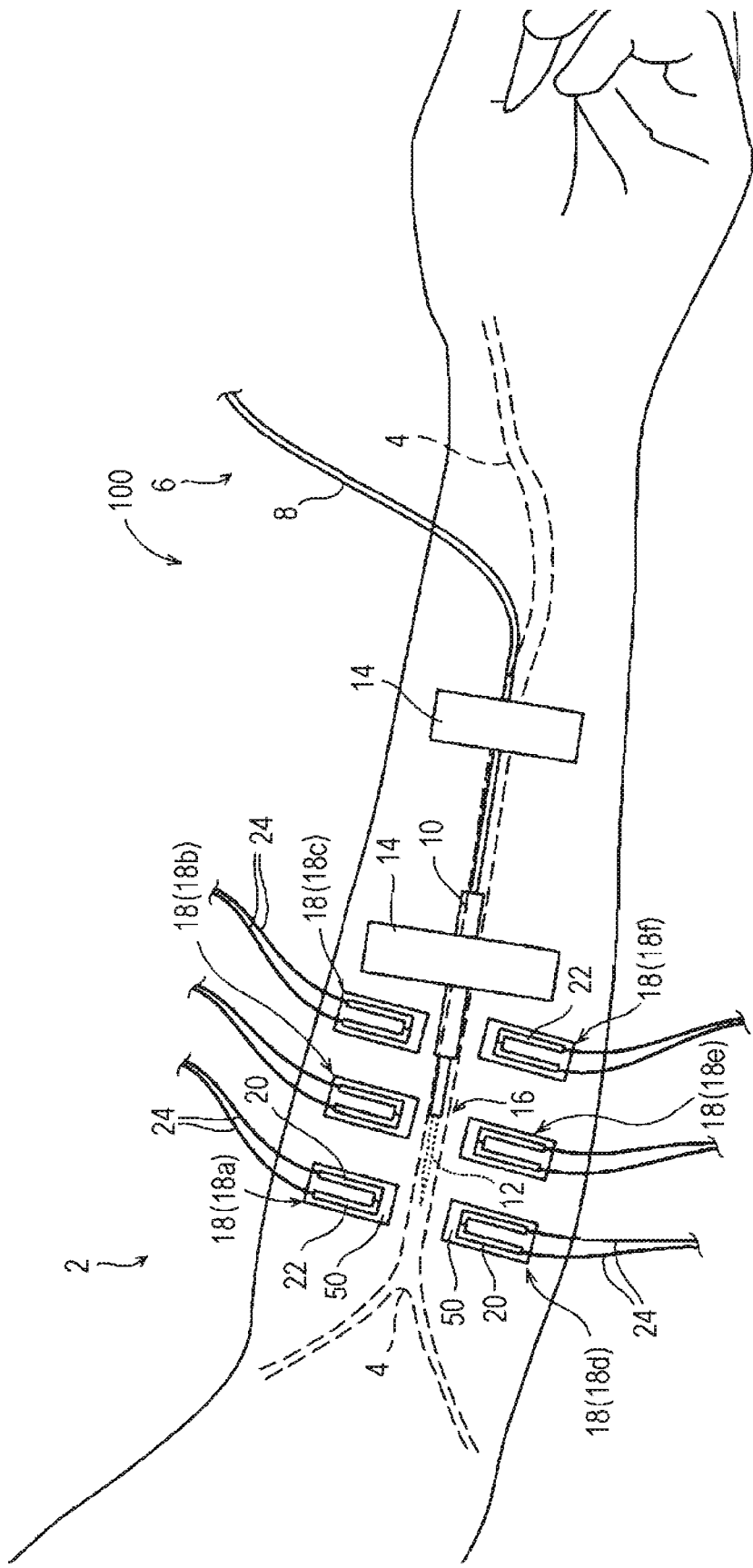
FIG. 1 is a view showing a mode of attachment of a thermocouple of a liquid leakage detection device according to embodiment 1.

As shown in FIG. 1, a liquid leakage detection device 2 according to embodiment 1 is used to detect that an injection solution such as an anticancer agent to be injected into a blood vessel 4 such as an arm leaks to the outside of the blood vessel 4 (hereinafter, referred to as "extravasation of injection solution"). The liquid leakage detection device 2 is used together with a drip infusion device 100 for injecting the injection solution into the blood vessel 4. The drip infusion device 100 includes a container (not shown) containing the injection solution and a transfusion set 6. The transfusion set 6 carries the injection solution from the container through an instrument such as a transfusion pump (not shown) or a transfusion controller (not shown) to a patient. In the transfusion set 6, a syringe 10 is connected to a distal end of a patient line 8 (a part between the instrument and the patient) which is a flow path of the injection solution. An injection needle 2 is punctured into the blood vessel 4 of the patient. The syringe 10 and a portion on the distal end side of the patient line 8 are fixed by a tape 14 so as to be along the patient's body surface.

Figure 3:
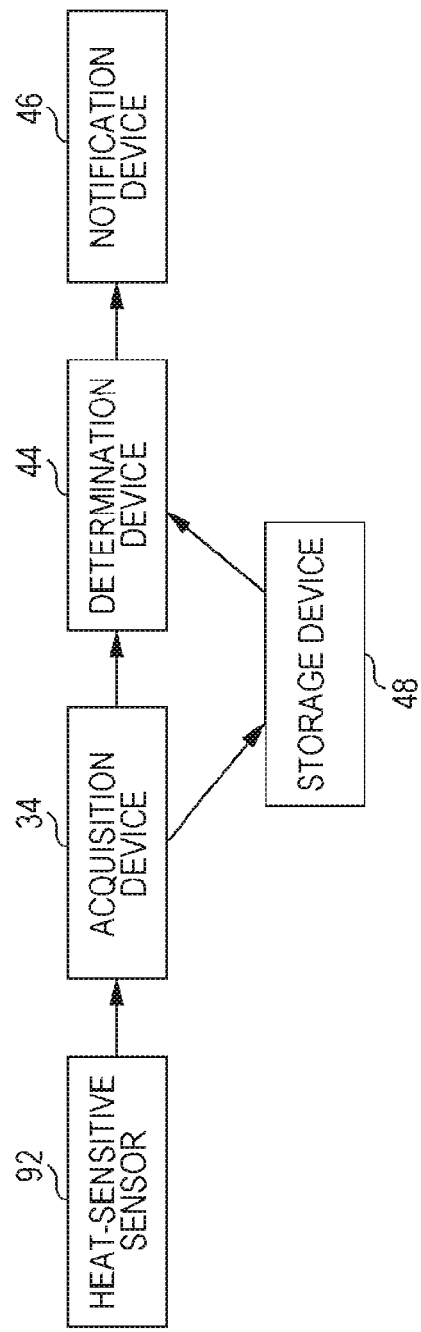
FIG. 3 is a block diagram of the liquid leakage detection device.

A heat-sensitive sensor 92 (FIG. 3) included in the liquid leakage detection device 2 has a plurality of (six in this example) thermocouples 18 which are heat-sensitive elements. Each of the thermocouples 18 is attached to the body surface. In this example, three heat-sensitive sensors 92 are respectively distributed and attached to both sides of the blood vessel 4 around a puncture site 16 punctured with the injection needle 12. The thermocouple 18 includes a positive side conductor 20, a negative side conductor 22, and a base sheet 50 made of an insulator for supporting the both conductors 20, 22 on the lower side. One end portion of the positive side conductor 20 and one end portion of the negative side conductor 22 are connected to each other and function as a temperature measuring junction 28. The thermocouple 18 is attached to the body surface by a double-sided tape or an adhesive provided on a lower surface of the base sheet 50. Therefore, the thermocouple 18 can sense a body surface temperature of an attachment point. The thermocouple 18 may include a cover sheet made of the insulator which seals to cover the both conductors 20, 22. Note that when distinguishing each of the thermocouples 18, alphabets (a to f) are attached.

Figure 2:
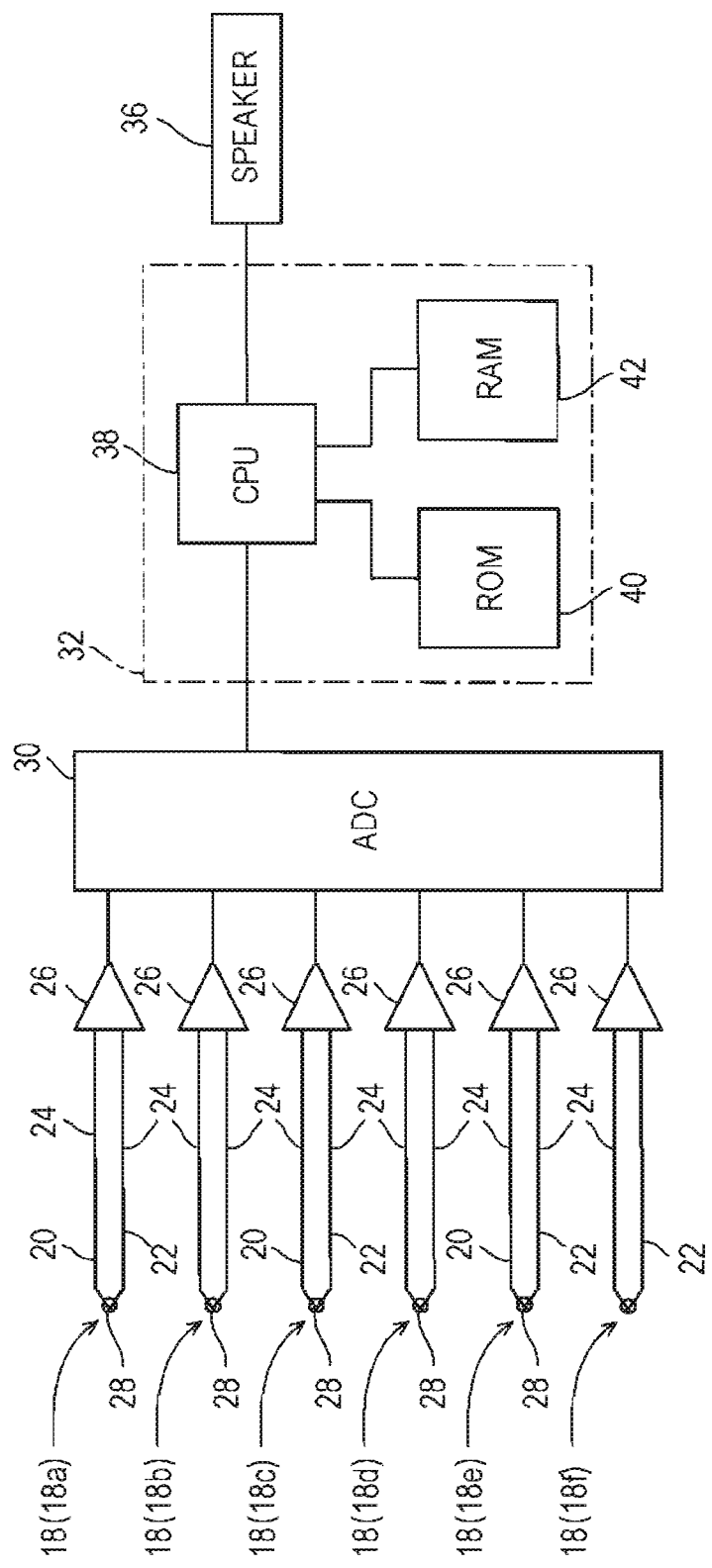
FIG. 2 is a hardware configuration diagram of the liquid leakage detection device.

As shown in FIG. 2, the positive side conductor 20 and the negative side conductor 22 of each thermocouple 18 are connected to an input of an amplifier circuit 26 via a compensating lead wire 24. Thus, a thermoelectromotive force generated at the temperature measuring junction 28 of each thermocouple 18 is input to the amplifier circuit 26. The amplifier circuit 26 amplifies the thermoelectromotive force so as to be suitable for an input range of an analog-to-digital conversion circuit (hereinafter referred to as "ADC", to which a reference numeral "30" is attached) to be described below.

An output of each amplifier circuit 26 is connected to the ADC 30. The ADC 30 is a circuit converting an analog signal input from the amplifier circuit 26 into a digital signal under control of a microcomputer 32 and is electrically connected to the microcomputer 32.

As will be described below, the microcomputer 32 causes the ADC 30 to perform the above conversion at a predetermined timing and receives the converted digital signal, thereby acquiring a value (hereinafter referred to as a "current temperature value") indicating the body surface temperature at that time. Therefore, the amplifier circuit 26, the ADC 30, and the microcomputer 32 function as an acquisition device 34 (FIG. 3) which acquires the current temperature value based on the thermoelectromotive force of each thermocouple 18.

The microcomputer 32 also has an output device shown) for outputting a sound signal. An alarm sound signal output from the output device is input to a speaker 36. The speaker 36 generates an alarm based on the input alarm sound signal and notifies that the extravasation has occurred. In this manner, the microcomputer 32 and the speaker 36 function as a notification device 46 (FIG. 3) for notifying that the extravasation has occurred.

The microcomputer 32 includes a central processing unit (hereinafter referred to as "CPU", to which a reference numeral "38" is attached), a ROM 40, and a RAM 42.

Programs are stored in the ROM 40. By executing this program by the CPU 38, an initialization process (FIG. 4), a detection process (FIG. 4), and a notification process (FIG. 4) to be described below are executed. In the detection process of the present embodiment, the body surface temperature at the attachment point of each of the thermocouples 18 is repeatedly sampled. Every time a sampling is performed, a difference (variation amount in the body surface temperature) between the body surface temperature obtained at that time and the body surface temperature obtained by the latest sampling is obtained. By comparing a difference between the variation amounts of each of the attachment points with a threshold value, it is checked whether the body surface temperature deviates from a normal temperature. When there is a deviation, it is determined that the extravasation has occurred. In this manner, the microcomputer 32 functions as a determination device 44 (FIG. 3) for determining the extravasation. Note that the normal temperature is the body surface temperature which naturally changes in the case where the extravasation does not occur.

The threshold value is a reference value for determining whether the body surface temperature sensed by any one of the plurality of thermocouples 18 deviates from the normal temperature. The threshold value is determined on the basis of results obtained by experimentally conducting drip infusion in advance and sampling the body surface temperature. Specifically, while confirming that no extravasation occurs, the body surface temperature is repeatedly sampled at a plurality of locations around the puncture site 16. The variation amount of the body surface temperature at each of the attachment points is calculated each time sampling, and the difference between the variation amounts at the attachment points is calculated in a round robin manner. The maximum value is extracted from a plurality of differences between the variation amounts obtained by repeating sampling, and this maximum value is determined as a threshold value. Note that when a cycle of sampling repeatedly performed is too short, variations in the body surface temperature do not significantly appear. When the cycle is too long, discovery of the extravasation will be delayed. Therefore, the cycle is determined so as to have an interval in which the variation of the body surface temperature significantly appears and the discovery of the extravasation is not delayed.

The RAM 42 has areas respectively storing (a) a variable $c[i]$ that stores the current temperature value at the attachment point of the thermocouple 18 acquired in sampling, (b) a variable $p[i]$ that stores a value (hereinafter referred to as the "latest temperature value") indicating the latest body surface temperature (acquired in the previous sampling) at the attachment point of the thermocouple 18, (c) a variable $f[i]$ that stores the variation amount of the body surface temperature at the attachment point of the thermocouple 18, (d) a variable "gap" that stores an absolute value of the difference between the variation amounts, and (e) a flag that indicates whether the extravasation occurs. Here, "i" takes values of "1" to "6". The values stored in each of the variables c[1] to c[6], the variables p[1] to p[6], and the variables f[1] to f[6] are values corresponding to the thermocouples 18a to 18f.

As described above, the ROM 40 and the RAM 42 function as a storage device 48 (FIG. 3) for storing the threshold value and each variable.

An operation flow of the microcomputer 32 will be specifically described below.

Figure 4:
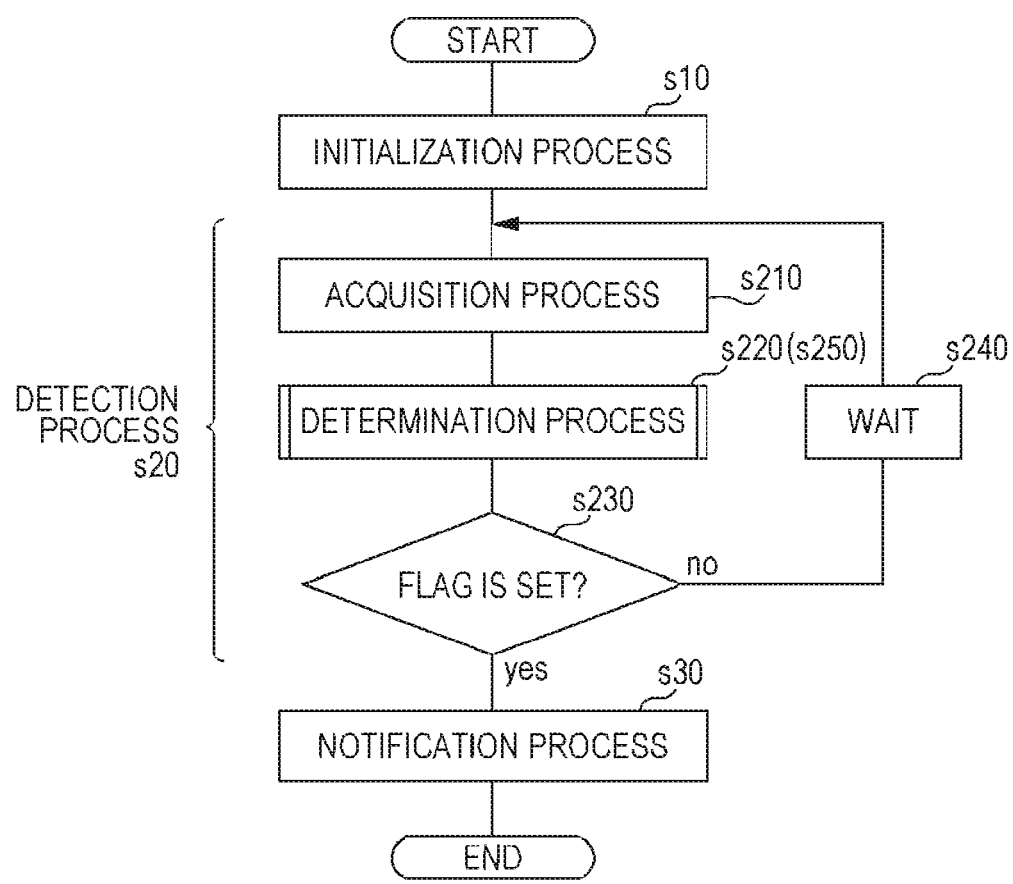
FIG. 4 is a flowchart showing an operation of the liquid leakage detection device.

When power is supplied to the microcomputer 32, as shown in FIG. 4, the CPU 38 of the microcomputer 32 executes the initialization process (s10) of storing an initial value in each variable included in the RAM 42. Specifically, an initial value "0" is stored in the variables c[1] to c[6], the variables f[1] to f[6], the variable "gap", and the flag. As the initial values of the variables p[1] to p[6], the current temperature values of the attachment points of the thermocouples 18a to 18f are stored. That is, the similar process as a current temperature value acquisition process (s210) to be described below is also executed in the initialization process (s10), and the current temperature value is acquired.

Next, the CPU 38 of the microcomputer 32 executes the detection process (s20). In this detection process (s20), the acquisition process (s210), a determination process (s220), and a flag check (s230) are executed in this order.

The acquisition process (s210) of the current temperature value is a process of acquiring the current temperature value of the attachment point of each of the thermocouples 18. Specifically, the CPU 38 inputs a conversion demand signal to the ADC 30. The conversion demand signal is a signal instructing the conversion of the analog signal. The ADC 30 converts the analog signal corresponding to the thermocouple 18a into the digital signal and outputs it. When the digital signal is input, the CPU 38 acquires the current temperature value by analyzing the digital signal and stores the current temperature value in the variable c[1]. The CPU 38 performs the processes on each of the signals corresponding to the thermocouples 18b to 18f. The CPU 38 stores the obtained current temperature values in the variables c[2] to c[6].

Figure 5:
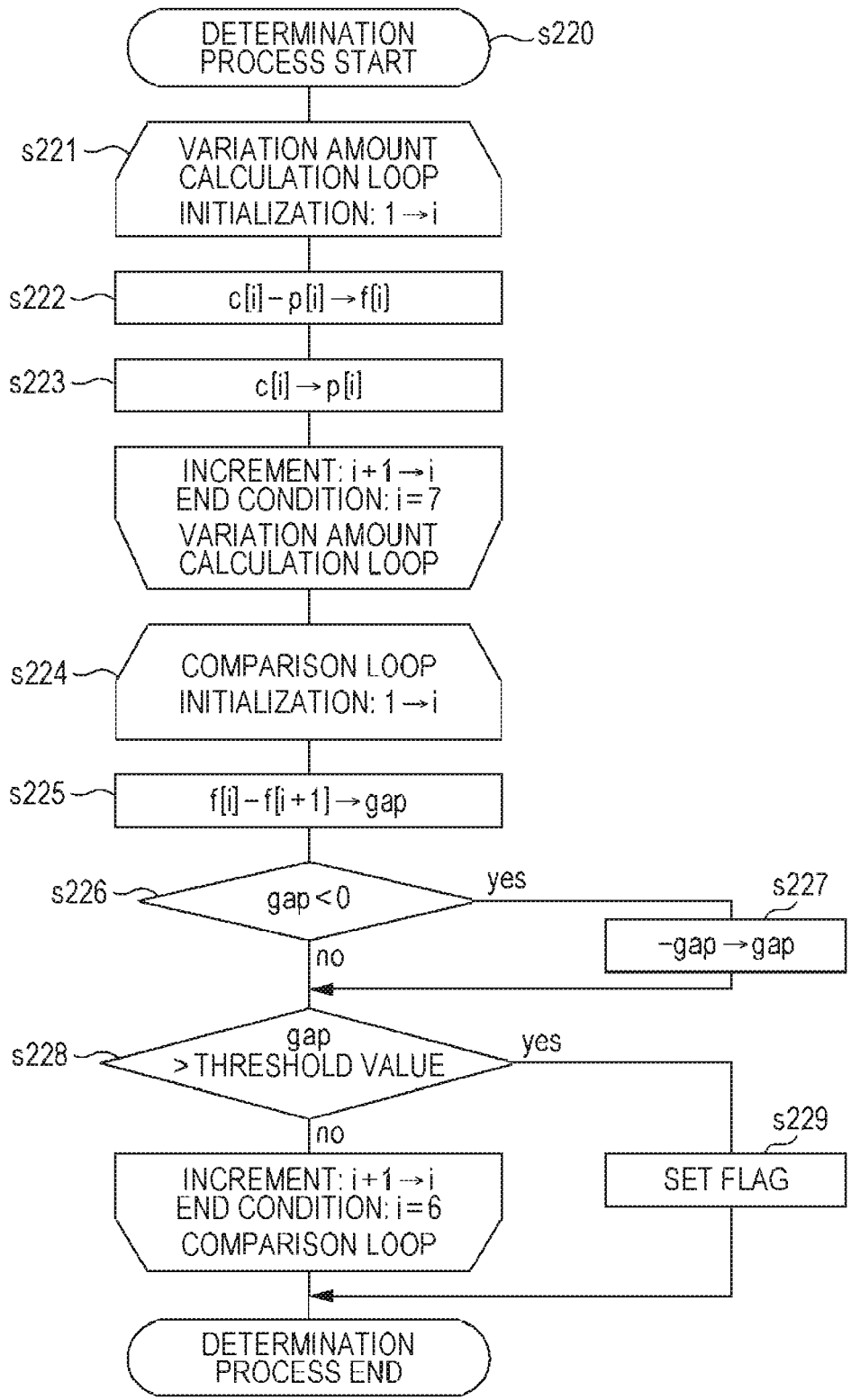
FIG. 5 is a flowchart showing a determination process in the above process.

In the determination process (s220), as shown in FIG. 5, the CPU 38 executes a variation amount calculation loop (s221). The variation amount calculation loop (s221) is a process for calculating the variation amount of the body surface temperature at the attachment point of the thermocouple 18. Specifically, the variation amount is obtained by subtracting the stored value (latest temperature value) of the variable p[i] from the stored value (current temperature value) of the variable c[i]. The variation amount is stored in the variable f[i] (s222). Next, in order to update the latest temperature value, a replacement process of storing the stored value of the variable c[i] in the variable p[i] is performed (s223). These processes are repeated until the value of is 1 to 6.

Next, the CPU 38 executes a comparison loop (s224). The comparison loop (s224) is a process of comparing each calculated variation amount with each other and checking whether the difference exceeds the threshold value. Specifically, it is as follows.

(1) An initial value of a loop variable "i" is set to "1" (s224).
(2) The difference between variation amounts is calculated by subtracting the stored value of variable f[i+1] from the stored value of variable f[i]. The difference is stored in the variable "gap" (s225).
(3) When the stored value of the variable "gap" is positive (s226: no), the process proceeds to comparison with the threshold value (s228).
(4) On the other hand, when the stored value of the variable "gap" is negative (s226: yes), a sign is inverted by multiplying the variable "gap" by −1. Thus, the absolute value of the difference between the variation amounts is stored in the variable "gap" (s227). Thereafter, the process proceeds to the comparison with the threshold value (s228).
(5) The stored value of the variable "gap" is compared with the threshold value (s228).
(6) As a result of the comparison, when the stored value of the variable "gap" is smaller than the threshold value (s228: no), the value of the loop variable "i" is incremented. The above processes (s225 to s228) are performed until the value is 6. When the value is 6, the determination process (s220) ends.
(7) On the other hand, as a result of the comparison, when the stored value of the variable "gap" is larger than the threshold value (s228: yes), it is determined that the body surface temperature deviates from the normal temperature, the flag is set (s229), and the determination process (s220) ends.

Returning to FIG. 4, after executing the determination process (s220), the CPU 38 checks whether the flag is set (s230). When the flag is not set (s230: no), it waits (s240) until the sampling cycle elapses and returns to the acquisition process (s210).

On the other hand, when the flag is set (s230: yes), the CPU 38 executes the notification process (s30). Specifically, the CPU 38 inputs the alarm sound signal for notifying extravasation through the output device to the speaker 36. Thus, an alarm sound is output from the speaker 36.

The liquid leakage detection device 2 having the above-described configuration can detect a reduction in the body surface temperature, which occurs when the injection solution having a temperature lower than the body temperature leaks to the outside of the blood vessel 4, by using the plurality of (six in this example) thermocouples 18. For example, when the extravasation occurs in the vicinity of the thermocouple 18d, the thermoelectromotive force of the thermocouple 18d is significantly reduced as compared with the thermoelectromotive force of the other thermocouples 18a to 18c, 18e and 18f. Then, the current temperature value corresponding to the thermocouple 18d is significantly lower than other values. Therefore, when the variation amount of the body surface temperature at the attachment point of each of the thermocouples 18a to 18f is calculated and the variation amounts are compared with each other, the difference between variation amounts corresponding to the other thermocouples 18a to 18c, 18e and 18f are small, however, the difference between the variation amount corresponding to the thermocouple 18d and the variation amount corresponding to the other thermocouple 18e increases and exceeds the threshold value. When the difference exceeds the threshold value, the flag is set and the alarm sound is output from the speaker 36 in the notification process (s30). Therefore, the patient and nurses can notice the extravasation.

According to the liquid leakage detection device 2 of the present embodiment, a plurality of thermocouples 18 is attached to the body surface around the puncture site 16. Thus, the body surface temperature around the puncture site can be directly sensed. Therefore, for example, even when the patient moves for picking up an object, or even when the puncture site 16 is covered with the bedding and the like, the body surface temperature can be normally sensed. Then, leakage of the injection solution is determined based on the body surface temperature. Therefore, a behavior of the patient receiving the drip infusion is not limited beyond necessity.

Embodiment 2

In embodiment 1, the heat-sensitive sensor 92 includes the plurality of thermocouples 18. In the liquid leakage detection device according to embodiment 2, the heat-sensitive sensor includes a single thermocouple 18. Hereinafter, configurations different from those of embodiment 1 will be described in detail, and description of common configurations will be omitted or briefly described.

In the liquid leakage detection device of embodiment 2, the thermocouple 18 is attached to an arbitrary point around the puncture site 16 of the injection needle 12. The thermoelectromotive force generated at the temperature measuring junction 28 of the thermocouple 18 is input to one of the amplifier circuits 26 via the compensating lead wire 24. The thermoelectromotive force amplified by the amplifier circuit 26 is converted into the digital signal by the ADC 30 and input to the microcomputer 32.

In the ROM 40 of the microcomputer 32, a program having a determination process different from that in embodiment 1 is stored. In the determination process (s250) (FIG. 6) of the present embodiment, the body surface temperature at the attachment point of the thermocouple 18 is repeatedly sampled to calculate an average body surface temperature. Every time the body surface temperature is sampled, the variation amount from the average body surface temperature is calculated. Whether the body surface temperature deviates from the normal temperature is checked based on whether the variation amount exceeds the threshold value. When there is a deviation, it is determined that the extravasation has occurred.

Regarding the threshold value, the body surface temperature around the puncture site 16 is repeatedly sampled while confirming experimentally that the extravasation does not occur in advance. Every time the sampling is performed, the variation amount of the body surface temperature is obtained. The maximum value among the plurality of variation amounts obtained in the experiment is determined as the threshold value.

The RAM 42 of the microcomputer 32 has areas respectively storing (a) a variable "c" that stores the current temperature value, (b) a variable "ave" that stores a value (hereinafter referred to as an "average temperature value") indicating an average value of the body surface temperature at the attachment point of the thermocouple 18, (c) a variable "f" that stores the variation amount of the current temperature value from the average temperature value, (d) a variable "n" that stores the number of calculation of the average temperature value, and (f) the flag.

When power is supplied to the microcomputer 32, the CPU 38 of the microcomputer 32 executes the initialization process (s10), the detection process (s20), and the notification process (s30) shown in FIG. 4.

In the initialization process (s10), "0" as the initial value is stored in the variable "c", the variable "ave", the variable "f", the variable "n", and the flag included in the RAM 42.

In the acquisition process (s210) of the detection process (s20), the current temperature value is acquired and stored in "c" as in embodiment 1.

Figure 6:
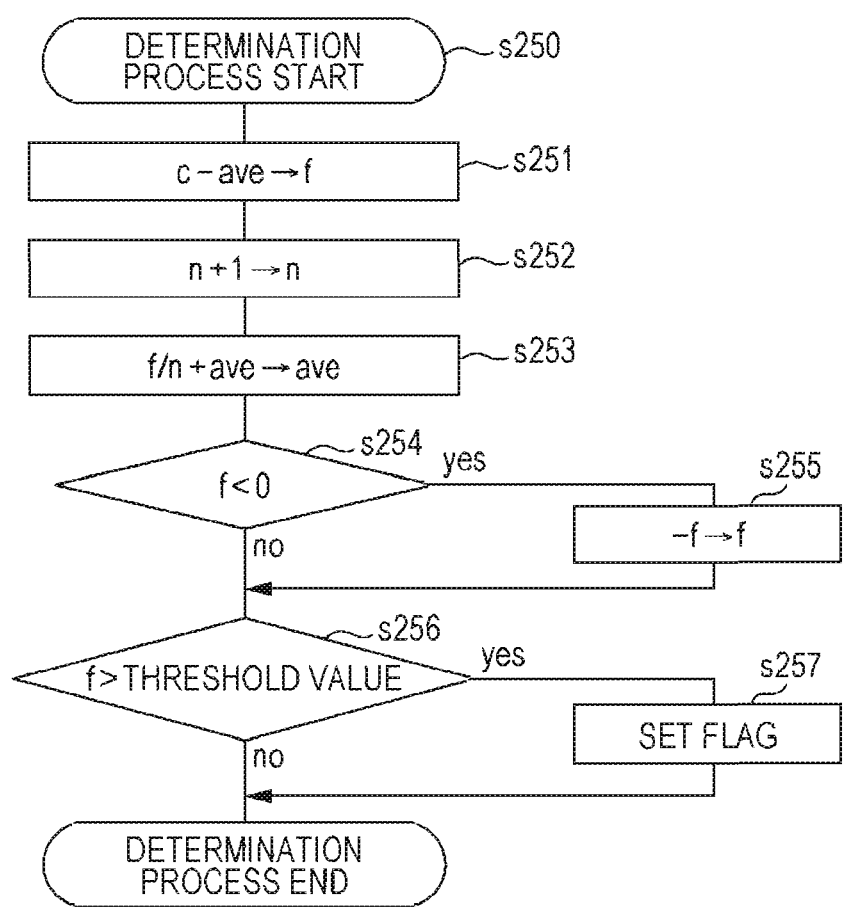
FIG. 6 is a flowchart showing the determination process of the liquid leakage detection device according to embodiment 2.

In the determination process (s250), specifically, the process is performed as shown in FIG. 6.

(1) The stored value (current temperature value) of the variable "c" is subtracted from the stored value (average temperature value) of the variable "ave", and the result is stored in the variable "f" (s251). Thus, the variation amount of the body surface temperature at the attachment point of the thermocouple 18 is stored in the variable "f".

(2) The stored value of the variable "n" is incremented (s252), and the stored value of the variable "n" is multiplied by 1/n to calculate the product. By adding the stored value of the variable "ave" to the product, the average temperature value is updated. The updated average temperature value is stored in the variable "ave" (s253).

(3) When the stored value of the variable "f" is positive (s254: no), the process proceeds to the comparison with the threshold value (s256).

(4) On the other hand, when the stored value of the variable "f" is negative (s254: yes), the variable "f" is multiplied by −1 and the result is stored in the variable "f" (s255). Thus, the absolute value of the variation amount is stored in the variable "f". Thereafter, the process proceeds to the comparison with the threshold value (s256).

(5) The stored value of the variable "f" is compared with the threshold value (s256).

(6) When the stored value of the variable "f" is smaller than the threshold value (s256: no), the determination process (s250) ends.

(7) When the stored value of the variable "f" is larger than the threshold value (s256: yes), it is determined that the body surface temperature deviates from the normal temperature, the flag is set (s257), and the determination process (s250) ends.

Returning to FIG. 4, after executing the determination process (s250), the CPU 38 checks a content of the flag. When the flag is not set (s230: no), the CPU 38 waits (s240) and then returns to the acquisition process (s210). On the other hand, when the flag is set (s230: yes), the CPU 38 inputs the alarm sound signal for notifying the extravasation through the output device to the speaker 36. Thus, the alarm sound is output from the speaker 36.

According to the liquid leakage detection device of the present embodiment, since there is only one thermocouple 18, it is possible to simplify the configuration of the device.

The liquid leakage detection device according to embodiments 1 and 2 has been described. The present invention is not limited to the above-described embodiments, but it may be modes described below as modifications.

(Modification 1)

In the determination process (s220) of embodiment 1, the variation amount of the attachment point of each of the thermocouples 18 may be calculated, and the maximum value and the minimum value of the variation amount may be obtained. Then, by determining whether the difference between the maximum value and the minimum value exceeds the threshold value, a significant variation of the body surface temperature may be examined. Further, in the determination process (s250) of embodiment 2, the latest temperature value of embodiment 1 may be calculated instead of the average temperature value, and the latest temperature value and the current temperature value may be compared. Then, the determination may be made based on whether the difference exceeds the threshold value.

(Modification 2)

Regarding the threshold value used in the determination process (s220, s250), for example, the extravasation may occur using the injection solution which is harmless to the human body and lower than the body temperature in the drip infusion experimentally performed in advance. Then, the body surface temperature before and after the extravasation may be sampled, and the determination may be made based on the variation amount of the body surface temperature.

(Modification 3)

In the liquid leakage detection device, a known reference junction compensator may be used in place of the ADC 30. An input of the reference junction compensator is connected to the thermocouple 18 via the compensating lead wire 24. An output of the reference junction compensator is connected to the microcomputer 32. In the present mode, the CPU 38 of the microcomputer 32 acquires the body surface temperature of the attachment point of each of the thermocouples 18 in the acquisition process (s210). The CPU 38 compares the acquired body surface temperature with the threshold value in the determination process (s220, s250). In the comparison, when the body surface temperature is lower than a lower limit value of the normal temperature or when the body surface temperature is higher than an upper limit value of the normal temperature, the CPU 38 determines that the body surface temperature deviates from the normal temperature and sets the flag.

(Modification 4)

The output device of the microcomputer 32 may output a video signal, and the liquid leakage detection device may be provided with a display connected to the output device. In the present mode, when the flag is set (s230: yes), the CPU 38 of the microcomputer 32 inputs the video signal for notifying the extravasation to the display through the output device. Thus, it is displayed that the extravasation has occurred on the display.

(Modification 5)

The output device of the microcomputer 32 may output a communication signal, and the liquid leakage detection device may have a network interface connected to the output device. In the present mode, when the flag is set (s230: yes), the CPU 38 of the microcomputer 32 outputs the communication signal for notifying the extravasation from the output device and transmits the communication signal via the network interface to an in-hospital terminal connected to the network. The in-hospital terminal includes, for example, a portable information terminal owned by a nurse or a nurse call terminal. Thus, it is possible to notify the nurse during patrol or the nurse waiting at a nurse station that the extravasation has occurred.

(Modification 6)

The heat-sensitive element 52 shown in FIG. 7 may be used. In the heat-sensitive element 52, a positive side conductor 56, an intervening film 58, a copper pad 60, and a negative side conductor 62 are laminated in this order on a tape-like base sheet 54 made of an insulator. An adhesive layer 64 is formed on the lower surface of the base sheet 54. The heat-sensitive element 52 is attached to the body surface by the adhesive layer 64.

The positive side conductor 56 is laminated over the entire upper surface of the base sheet 54. One end portion of an upper surface of the positive side conductor 56 is exposed. The compensating lead wire 24 on the positive side is connected to this exposed portion 66.

The intervening film 58 is made of a resin such as polyimide. The intervening film 58 is laminated on the upper surface of the positive side conductor 56 with the exposed portion 66 of the positive side conductor 56 therebetween. The intervening film 58 has a rectangular shape each side of which is substantially equal to a width of the positive side conductor 56, and its typical thickness is 50 μm.

A copper pad 60 is laminated on a central portion of an upper surface of the intervening film 58. The copper pad 60 is connected to the negative side compensating lead wire 24.

The negative side conductor 62 extends linearly from a center portion of an upper surface of the copper pad 60 to the other end portion of the positive side conductor 56.

With the heat-sensitive element 52 having the above structure, a contact surface between the positive side conductor 56 and the negative side conductor 62 is long, and the Seebeck effect occurs on the entire contact surface. Therefore, the contact surface can function in the same way as the temperature measuring junction of the thermocouple. By attaching such a heat-sensitive element 52 along the blood vessel 4, it is possible to sense the body surface temperature in a wide range (long range) along the blood vessel 4.

(Modification 7)

A heat-sensitive sensor 90 shown in FIG. 8(*a*) may be used. In the heat-sensitive sensor 90, a plurality of (six in this example) temperature measuring junctions 74 is provided on a base sheet 68 made of an insulator extending across the blood vessel 4. An adhesive layer (not shown) is formed on a lower surface of the base sheet 68. The heat-sensitive sensor 90 is attached to the body surface by the adhesive layer.

The base sheet 68 has a pair of tape portions 70 arranged on both sides of the blood vessel 4 and extending along the blood vessel 4 and a connecting portion 72 connecting one end sides of the pair of tape portions 70. A gap is formed between the other end sides of the pair of tape portions 70. The syringe 10 is disposed in the gap.

The plurality of (six in this example) temperature measuring junctions 74 is distributed and arranged in each of the pair of tape portions 70. Each of the temperature measuring junctions 74 is formed by a positive side conductor 76 and a negative ide conductor 78. Each of the positive side conductors 76 and each of the negative ide conductors 78 are formed in a hook shape so as to extend inwardly from a plurality of copper pads 60 formed at an edge of the base sheet 68 and so that tip ends of the positive side conductor 76 and the negative side conductor 78 overlap each other.

The heat-sensitive sensor 90 of FIG. 8(*a*) is convenient because the plurality of temperature measuring junctions 74 can be attached to the body surface in a single operation.

(Modification 8)

The heat-sensitive sensor 88 shown in FIG. 8(*b*) may be used. In the heat-sensitive sensor 88, a positive side conductor 82 and a negative side conductor 86 are laminated in this order on the pair of tape portions 70 and the connecting portion 72 of a base sheet 96 made of the insulator extending across the blood vessel 4. The adhesive layer (not shown) is formed on a lower surface of the base sheet 96. The heat-sensitive sensor 88 is attached to the body surface by the adhesive layer.

The base sheet 96 has a terminal portion 80 in addition to the pair of tape portions 70 and the connecting portion 72. On the terminal portion 80, the positive side conductor 82, the intervening film 58, the copper pad 60, and the negative side conductor 86 are laminated in this order. An end portion of the positive side conductor 82 is exposed. The exposed portion 84 is connected to the positive side compensating lead line 24.

With the heat-sensitive sensor 88 of the above mode, the positive side conductor 82 and the negative side conductor 86 are in contact with each other over substantially the entire upper surface of the base sheet 96 (the pair of tape portions 70 and the connecting portion 72). The Seebeck effect occurs on the entire surface of the contact portion. Therefore, the contact portion can function in the same manner as the temperature measuring junction of the thermocouple. By attaching such a heat-sensitive sensor 88 to the vicinity of the puncture site 16, it is possible to sense the body surface temperature on substantially the entire surface of the body surface around the puncture site 16. Therefore, it is possible to reduce omission of detection of the extravasation.

(Modification 9)

The following materials or forming methods can be used for the thermocouple 18, the heat-sensitive element 52, and the heat-sensitive sensors 88, 90 described in the above embodiments and the modifications 6 to 8.

The base sheets 50, 54, 68 and 96 are, for example, resin films or nonwoven fabrics having a thickness of about 50 μm. In addition, the material of the base sheets 50, 54, 68 and 96 is typically an elastomer, and the elastomer includes, for example, polyimide and silicone.

The positive side conductors 20, 56, 76 and 82 are copper patterns formed on the base sheets 50, 54, 68 and 96. The copper pattern is formed by etching, printing copper paste, or attaching a copper foil. A thickness of the copper pattern formed by etching is typically 9 μm. The thickness of the copper pattern formed by printing the copper paste is typically 250 μm. The thickness of the copper pattern formed by the copper foil is typically 36 μm.

The negative side conductors 22, 62, 78 and 86 are constantan powder-containing conductive patterns formed on the base sheets 50, 54, 68 and 96. The constantan powder-containing conductive pattern is formed by printing a conductive paste containing constantan powder on the base sheets 50, 54, 68 and 96. Its thickness is typically 250 μm. Composition of the constantan powder is 55±5% copper and 45±5% Ni. An average particle diameter of the constantan powder is 1 to 50 μm. Binder components used for the conductive paste includes alkylene glycol diglycidyl ether. Thus, flexibility is given to the conductive paste. A content of the alkylene glycol diglycidyl ether is preferably 5 mass % or more, more preferably 10 to 80 mass % in the binder components. Specifically, as the alkylene glycol diglycidyl ether, known polyethylene glycol diglycidyl ether or propylene glycol diglycidyl ether can be used. An epoxy resin or a (meth) acrylate compound may be added to the binder component used for the conductive paste as needed.

The thermocouple 18, the heat-sensitive element 52, and the heat-sensitive sensors 88, 90 having the above-described structure have flexibility, and when attached to the body surface, floating and detachment of the beat-sensitive portion (temperature measuring junction) is unlikely to occur and adhesion to the body surface is good. Therefore, measurement accuracy of the body surface temperature can be improved.

(Modification 10)

The thermocouple 18, the heat-sensitive element 52, and the heat-sensitive sensors 88, 90 described in the above embodiments and the modifications 6 to 8 may be attached so that the temperature measuring junctions 28, 74 or portions functioning similarly to the temperature measuring junctions are in direct contact with the body surface.

(Modification 11)

The heat-sensitive sensor 92 of the present invention may be constituted by one or more thermistors or one or more known semiconductor temperature sensors.

The present invention can be carried out in a mode in which various improvements, modifications, and variations are added based on knowledge of those skilled in the art without departing from the spirit of the invention, and all of these aspects belong to the range of the present invention. The present invention can be variously modified without departing from the spirit of the present invention.

LIST OF REFERENCE NUMERALS

2: Liquid leakage detection device
4: Blood vessel
18: Thermocouple
52: Heat-sensitive element
88, 90: Heat-sensitive sensor
92: Heat-sensitive sensor
34: Acquisition device
44: Determination device

The invention claimed is:

1. A liquid leakage detection device for detecting that an injection solution to be injected into a blood vessel leaks to the outside of the blood vessel, comprising:
   a heat-sensitive sensor to be attached to a body surface around a puncture site of an injection needle for injecting the injection solution;
   an acquisition device which acquires a value indicating a body surface temperature at an attachment point of the heat-sensitive sensor based on an output of the heat-sensitive sensor; and
   a determination device which determines that the injection solution leaks to the outside of the blood vessel when the acquired value deviates from a normal temperature of the body surface temperature at the attachment point, wherein
   the heat-sensitive sensor is a plurality of heat-sensitive elements,
   the plurality of heat-sensitive elements is configured to be distributed and attached of the blood vessel into which the injection needle is punctured,
   the attachment point is a plurality of attachment points, and
   the determination device:
      calculates a variation amount of the body surface temperature attachment points, the variation amount being a difference between the value currently acquired by the acquisition device at the respective attachment point and the value previously acquired by the acquisition device at the respective attachment point;
      calculates a difference between the variation amounts of each of the plurality of attachment points;
      compares the difference between the variation amounts with a threshold value; and
      determines that the injection solution leaks to the outside of the blood vessel based on a result of the comparison in which the difference is larger than the threshold value.

2. The liquid leakage detection device according to claim 1, further comprising a notification device which notifies that the injection solution leaks to the outside of the blood vessel when the determination device determines that the injection solution leaks to the outside of the blood vessel.

3. A liquid leakage detection device for detecting that an injection solution to be injected into a blood vessel leaks to the outside of the blood vessel, comprising:
- a heat-sensitive sensor to be attached to a body surface around a puncture site of an injection needle for injecting the injection solution;
- an acquisition device which acquires a value indicating a body surface temperature at an attachment point of the heat-sensitive sensor based on an output of the heat-sensitive sensor; and
- a determination device which determines that the injection solution leaks to the outside of the blood vessel when the acquired value deviates from a normal temperature of the body surface temperature at the attachment point, wherein the heat-sensitive sensor is a single heat-sensitive element, the acquisition device repeatedly samples the body surface temperature at the attachment point, and the determination device:
- calculates an average body surface temperature from the body surface temperature repeatedly sampled by the acquisition device;
- calculates a variation amount which is a difference between the value currently acquired by the acquisition device at the attachment point and the average body surface temperature;
- compares the variation amount with a threshold value; and
- determines that the injection solution leaks to the outside of the blood vessel based on a result of the comparison in which the variation amount is larger than the threshold value.

4. The liquid leakage detection device according to claim 3, further comprising a notification device which notifies that the injection solution leaks to the outside of the blood vessel when the determination device determines that the injection solution leaks to the outside of the blood vessel.

* * * * *